(12) United States Patent
Howard et al.

(10) Patent No.: US 8,128,955 B2
(45) Date of Patent: Mar. 6, 2012

(54) FOOD COMPOSITIONS CONTAINING CREATINE

(75) Inventors: Alan N. Howard, Great Shelford (GB); Roger C. Harris, Suffolk (GB)

(73) Assignee: The Original Creatine Patent Company (GB)

( * ) Notice: Subject to any disclaimer, the term of this patent is extended or adjusted under 35 U.S.C. 154(b) by 1092 days.

(21) Appl. No.: 10/855,317

(22) Filed: May 28, 2004

(65) Prior Publication Data

US 2005/0008678 A1 Jan. 13, 2005

Related U.S. Application Data

(63) Continuation-in-part of application No. 10/368,427, filed on Feb. 20, 2003, now Pat. No. 7,150,880, which is a continuation-in-part of application No. 09/917,634, filed on Jul. 31, 2001, now Pat. No. 6,524,611, and a continuation-in-part of application No. 09/419,922, filed on Oct. 18, 1999, now Pat. No. 6,274,161, which is a continuation-in-part of application No. 08/866,517, filed on May 30, 1997, now Pat. No. 5,968,544.

(30) Foreign Application Priority Data

May 31, 1996 (GB) .................................. 9611356.8
Mar. 2, 2001 (GB) .................................. 0105205.9

(51) Int. Cl.
*A61K 47/00* (2006.01)
*A23B 7/148* (2006.01)
*B65B 55/00* (2006.01)

(52) U.S. Cl. ......... 424/439; 426/106; 426/128; 426/392

(58) Field of Classification Search .................... 424/27, 424/439; 514/69; 426/72, 93, 535, 599
See application file for complete search history.

(56) References Cited

U.S. PATENT DOCUMENTS

| | | | |
|---|---|---|---|
| 2,919,195 A * | 12/1959 | Block | 426/72 |
| 3,615,600 A | 10/1971 | Tonsbeek | |
| 3,978,240 A * | 8/1976 | van der Heijden et al. | 426/535 |
| 4,371,521 A | 2/1983 | Izrael | |
| 4,464,409 A | 8/1984 | de Rooij | |
| 4,647,453 A | 3/1987 | Meisner | |
| 4,673,578 A * | 6/1987 | Becker et al. | 426/93 |
| 4,772,591 A | 9/1988 | Meisner | |
| 5,077,313 A | 12/1991 | Lubec | |
| 5,091,404 A | 2/1992 | Elgebaly | |
| 5,162,128 A * | 11/1992 | Mills et al. | 426/599 |
| 5,308,627 A | 5/1994 | Umbdenstock, Jr. | |
| 5,332,579 A | 7/1994 | Umbdenstock | |
| 5,391,550 A | 2/1995 | Carniglia et al. | |
| 5,397,786 A | 3/1995 | Simone | |
| 5,767,159 A | 6/1998 | Hultman et al. | |
| 5,773,473 A | 6/1998 | Green et al. | |
| 5,908,864 A | 6/1999 | Casey | |
| 5,968,544 A | 10/1999 | Howard et al. | |
| 6,075,031 A | 6/2000 | Kaddurah-Daouk et al. | |
| 6,117,872 A * | 9/2000 | Maxwell et al. | 514/249 |
| 6,168,802 B1 | 1/2001 | Howard et al. | |
| 6,274,161 B1 | 8/2001 | Howard et al. | |
| 6,524,611 B2 | 2/2003 | Howard et al. | |
| 2001/0008641 A1 | 7/2001 | Krotzer | |
| 2003/0219500 A1 | 11/2003 | Howard et al. | |
| 2004/0137112 A1 | 7/2004 | Katz et al. | |
| 2005/0112177 A1* | 5/2005 | Dopson et al. | 424/439 |

FOREIGN PATENT DOCUMENTS

| | | |
|---|---|---|
| EP | 0199117 A2 | 10/1986 |
| EP | 0222257 A2 | 5/1987 |
| EP | 0449787 A2 | 10/1991 |
| EP | 0669083 A2 | 8/1995 |
| GB | 2313544 A | 12/1997 |
| JP | 59025663 | 2/1984 |
| JP | 50087771 | 9/1996 |
| WO | WO94/02127 | 2/1994 |
| WO | WO94/15488 | 7/1994 |
| WO | WO94/17794 | 8/1994 |
| WO | WO96/04240 A1 | 2/1996 |
| WO | WO96/14063 | 5/1996 |
| WO | WO96/36348 | 11/1996 |
| WO | WO97/45026 | 12/1997 |
| WO | WO 98/53704 * | 3/1998 |
| WO | WO98/53704 | 12/1998 |
| WO | WO00/74500 A1 | 12/2000 |
| WO | 01/33976 | 5/2001 |
| WO | 01/70238 | 9/2001 |
| WO | WO02/069740 A | 9/2002 |

OTHER PUBLICATIONS

Herman et al. "Limonoid Glucosides in Orange Juices by HPLC"; Journal of Agricultural Food Chemistry 1990 (38), pp. 1860-1861.*
Website: www.glycemicindex.com (see interactive database for "juices".*
http://karosyrup.com/products.html; website demonstrating that corn syrup may or may not have fructose.*
Foster-Powell et al. (Am J Clin Nutr; 2002; 76:5-56).*
2000 Animal Nutrition Symposia, Laboratory Animal Care Course, PMI Nutrition International, Lab Diet 5001, 1996, www.labdiet.com. home.htm.
Edgar et al., "The Equilibrium Between Creatine and Creatinine, in Aqueous Solution. The Effect of Hydrogen Ion", J. Am. Chem. Soc. 47, 1179-1188, (1925).
Cannan et al," CXV, The Creatine-Creatinine Equilibrium. The Apparent Dissociation Constants of Creatine and Creatinine", Biochem J., 22, 920-929, (1928).
Acito, et al., "Valutazione Degli Effetti Emodinamici Dell'infusione Acuta e Per Trattamento a Breve Termine di Creatina Fosfato", Clin. Ter., 111, 427-433 (1984). Statement of Relevancy Provided.
Marchetti, et al., "Studio Elettromiografico del Trattamento Protratto con Fosfocreatina in Affezioni Neuromuscolari", Clin. Ter., 114, 489-494 (1985). Statement of Relevancy Provided.
Moerland, et al., "Administration of a Creatine Analog Induces Isomyosin Transitions in Muscle", 13—Mammalian Biochem., vol. 111, p. 517 (1989).

(Continued)

*Primary Examiner* — S. Tran
*Assistant Examiner* — Jeffrey T Palenik
(74) *Attorney, Agent, or Firm* — Patton Boggs LLP

(57) ABSTRACT

Disclosed is a solid or semi-solid foodstuff for human consumption, the foodstuff comprising creatine suspended in solid form in an edible supporting matrix; the foodstuff being in the form of a bar.

18 Claims, No Drawings

OTHER PUBLICATIONS

Borgoglio, et al., "Time-course of the Effect of Intravenously Administered Phosphocreatine on ATP and CP Concentrations in Rat Heart", Chemical Abstracts, vol. 99, p. 430 (1983).

Vandenberghe, et al., "Caffeine Counteracts the Ergogenic Action of Muscle Creatine Loading", J. Appl. Physiol. 80, 2, 452-457 (1996).

Harris., et al. "Glycogen, Glycolytic Intermediates and High-Energy Phosphates Determined in Biopsy Samples of Musculus Quadriceps Femoris of Man at Rest. Methods and Variance of Values", Scand. J. Clin. Lab. Invest., 33, 109-120 (1974).

Dunnett, et al., "Reverse-Phase Ion-Pairing High-Performance Liquid Chromatography of Phosphocreatine, Creatine and Creatinine in Equine Muscle", Scand. J. Clin. Lab. Invest., 51, 137-141 (1991).

Graham, T., "Caffeine and Exercise Metabolism, Endurance and Performance", Sports Med., 31(11), 785-807 (2001).

McCarty, M. F., "Nutraceutical resources for diabetes prevention—an update", Medical Hypotheses, 2005, pp. 151-158, vol. 64, Eden Press, Penrith, US.

International Search Report issued in International Application No. PCT/GB2005/002127 on May 28, 2004, (5 pages).

* cited by examiner

FOOD COMPOSITIONS CONTAINING CREATINE

This application is a Continuation-In-Part of U.S. application Ser. No. 10/368,427, filed Feb. 20, 2003, now U.S. Pat. No. 7,150,880 which is a Continuation-In-Part of U.S. application Ser. No. 09/917,634, filed Jul. 31, 2001 (which issued as U.S. Pat. No. 6,524,611 on Feb. 25, 2003), which derives priority from Great Britain Application No. 0105205.9 and is a Continuation-In-Part of U.S. application Ser. No. 09/419,922, filed Oct. 18, 1999 (which issued as U.S. Pat. No. 6,274,161 on Aug. 14, 2001), which is a Continuation-In-Part of U.S. application Ser. No. 08/866,517, filed May 30, 1997, which issued as U.S. Pat. No. 5,968,544 on Oct. 19, 1999, which derives priority from Great Britain Application No. 9611356.8, filed May 31, 1996. The entirety of all the above applications are incorporated herein by reference.

Related U.S. application Ser. No. 09/324,119, which issued as U.S. Pat. No. 6,168,802 on Jan. 2, 2001, which is a Continuation-In-Part of U.S. application Ser. No. 08/866,517 and issued as U.S. Pat. No. 5,968,544 on Oct. 19, 1999 is fully incorporated herein by reference.

BACKGROUND OF THE INVENTION

1. Field of the Invention

This invention relates to food compositions for human consumption comprising creatine and to a method of providing such compositions.

2. Background of the Technology

In the last few years there has been considerable interest among athletes in creatine, which occurs abundantly in skeletal muscle. Creatine plays a pivotal role in the regulation and homeostasis of skeletal muscle energy metabolism and it is now generally accepted that the maintenance of phosphocreatine availability is important to the continuation of muscle force production. Creatine may also be involved in other processes concerned with protein synthesis and hypertrophy of muscle fibres during training. Although creatine synthesis occurs in the liver, kidney and pancreas it has been known for some time that the oral ingestion of creatine will add to the whole body creatine pool, and it has been shown that the ingestion of 20 to 30 g creatine monohydrate ($Cr.H^2O$) per day for several days can lead to a greater than 20% increase in human skeletal muscle total creatine content. Thus, WO94/02127 discloses the administration of creatine monohydrate in amounts of at least 15 g (or 0.2-0.4 g/kg body weight) per day, for at least 2 days, for increasing muscular strength.

In fact, it was subsequently found that after several days of supplementation (20 g per day) with creatine monohydrate in order to attain initial elevation of the tissue stores, thereafter it takes no more than 2 to 3 g per day to maintain the newly elevated concentration. Supplementation with any bioavailable source of creatine (i.e. creatine supplementation) in an appropriate dose can provide improvements to athletes involved in explosive events, which include all events lasting from a few seconds to a few minutes (such as sprinting, swimming, weight-lifting etc). Endurance performance in events lasting longer than about 30 minutes appear less affected by creatine supplementation except where this involves short periods of increased energy output particularly when the local muscle carbohydrate stores have become depleted. Creatine is a normal food component and is not a drug and its use is not contrary to official regulations. It is possible that the greatest benefits of creatine supplementation are experienced by the elderly, vegetarians or those who eat no meat or fish, since these people tend to have low muscle creatine contents. Also, recent studies have shown that creatine can reduce mental fatigue (Watanabe et al., Neuroscience Research, 42 (2002) 279-285).

Furthermore, creatine and its derivatives have been used in the past for the preparation of products with a meaty or savory flavor. For instance, Tonsbeek (U.S. Pat. No. 3,615,600) discloses and is concerned with artificial flavoring, describing mixtures imparting a meaty flavor to foods. Similarly de Rooji (U.S. Pat. No. 4,464,409) is concerned with meat flavoring. Yamazaki (JP-A-59035663) prepares a meat flavor by heating a mixture comprising creatine at pH 5.0-7.0 at a temperature of 80-130° C. for 30-120 minutes. Under these conditions most of the creatine is converted to creatinine.

The inventors believe that it would not occur to the persons skilled in the art to add creatinine (used hitherto as a meat or savory flavoring agent) to compositions which were intended to have a flavor (especially a fruit flavor) other than meaty or savory. The person skilled in the art might have expected the addition of creatinine to result in an unpalatable combination of fruit and meat flavors, whereas in fact the inventors have found that the resulting combination does not impart an undesirable meaty flavor.

WO 97/45026 discloses an acidic composition for human consumption comprising creatine and its derivatives, the composition being provided as a dry powder or in liquid or semi-liquid form. The compositions disclosed therein are stable at refrigerated temperatures (4° C.) for prolonged periods but stable at ambient temperature for relatively short periods (e.g., up to, but not exceeding, 7 days).

WO 00/74500 discloses compositions comprising creatine and its derivatives suspended in aloe vera gel, which compositions were stable (with respect to the conversion of creatine to creatinine) at room temperature for 2 weeks or more, depending on the initial concentration of creatine in the composition.

Both WO 97/45026 and WO 00/74500 stress the desirability of preventing the conversion of creatine to creatinine.

SUMMARY OF THE INVENTION

In a first aspect the invention provides a solid or semi-solid foodstuff, the foodstuff comprising creatine suspended in solid form in an edible supporting matrix; the foodstuff being in the form of a bar.

Also provided is a solid or semi-solid foodstuff that includes from 0.5 to 200 g of creatine per Kg of prepared foodstuff composition, the foodstuff being formed as a bar.

Also provided is a solid or semi-solid foodstuff that includes between 5 g and 200 g stable creatine in a supporting food-stuff matrix that can include viscosity modifiers, other nutrients, pH stabilizers, raising agents, vitamins, minerals, flavorings, and/or preservatives, the foodstuff product being formed as a bar.

Also provided is a solid or semi-solid foodstuff that includes from 0.5 to 200 g of creatine per Kg of prepared foodstuff composition, and at least one carbohydrate source having a low glycemic index, the foodstuff being formed as an individual-serving bar.

DETAILED DESCRIPTION OF THE INVENTION

The present invention is described in detail below with the use of non-limiting examples, which serve to demonstrate compositions and manufacturing process that fall within the scope of the invention as defined by the attached claims.

The creatine bar product of the present invention provides an individual-size portion of an effective creatine product that can be configured and packaged into a commercially-accepted conventional form such as a nutrient bar or health bar. The creatine content may be present as crystals, powder or the like, and is distributed within the edible supporting matrix, which may be a viscous liquid or semi-liquid or a solid, typically such that settling of the solid creatine (under the influence of gravity) is inhibited or prevented.

The creatine content of the composition may be present as any active form of creatine (e.g. creatine phosphate and other bioavailable creatine salts), but creatine monohydrate is found particularly convenient as a source of creatine. The creatine content of the composition is preferably subjected to a micronization process (e.g., crushing, pulverizing, powdering and the like) prior to incorporation into the matrix, so that the resulting composition is not unacceptably "gritty" in texture.

Preferably the creatine will be distributed substantially evenly throughout the supporting matrix (by homogenizing in some manner e.g. by mixing, stirring, blending and the like), which may be accomplished manually and/or mechanically at the time the composition is prepared.

Conveniently the supporting matrix is, or comprises, a recognized foodstuff, such that a composition in accordance with the invention may take the form of an otherwise conventional foodstuff, supplemented with creatine, such that solid creatine becomes suspended in the foodstuff. Examples of foodstuffs which may represent suitable supporting matrices for the composition of the invention include spreadable solids such as fat, butter, margarine and the like. Other convenient supporting matrices are those comprising sugars or other carbohydrates, such as liquid ("runny") or solid ("set") honey, molasses, syrup (e.g., corn syrup, glucose syrup), treacle or "Maxim Energy Gel"™. Fat, butter or margarine and the like are preferred, as they can also serve to bind the ingredients together.

If desired, the viscosity of the edible matrix and/or the composition as a whole, may be increased by the addition of viscosifiers, gelling agents and the like. Such components are well-known in the foods industry and include, for example, plant-derived polysaccharides, gums and the like such as galactomannans, dextrans, guar gum, locust beam gum and so on. One suitable edible matrix comprises a gel prepared from concentrated Aloe Vera extract: a smooth creamy paste (suitable for packaging in a squeezable tube) may be prepared by mixing 5 gms of creatine with 20 mls of a concentrated Aloe Vera gel (such as that obtainable from Aloe Commodities Int. Inc., Farmers Branch, Tex. 75234).

The present inventors have previously found that the conversion of creatine to creatinine in acidic aqueous solutions can be markedly inhibited by storage of creatine-containing solutions below ambient temperature. The inventors have now found that, by providing creatine in the form of a suspension, rather than in solution, conversion to creatinine (even in an acidic composition) can be greatly inhibited or even substantially prevented even at ambient (i.e., 20-25° C.) temperature. Thus, in some embodiments the composition as a whole (and/or the supporting matrix in isolation) may conveniently be selected to be any pH, acidic (i.e., have a pH below 7.0) or alkaline (pH 7.0-8.5), without significantly adversely affecting the stability of the creatine content of the composition. In particular the composition desirably has a pH between 3.0 and 8.5, preferably between 3.5 and 8.0. In some embodiments the composition may have a pH in the range 3.5-5.5 which, to the human palate, has a refreshingly sharp taste without being too acidic.

Compositions in accordance with the invention are substantially stable so that creatine may be presented in acidic formulations, contrary to the teaching of the art, in physiologically useful amounts, even following storage for prolonged periods at ambient temperature. A physiologically useful amount of creatine is an amount sufficient to cause a measurable increase in the creatine content of the tissues of a subject following repeated consumption of the composition, relative to an initial baseline level.

The term "substantially stable" is herein defined as referring to a composition in which at least 85% of the original creatine in the composition is unchanged into creatinine for a period of at least 7 days storage at ambient (20-25° C.) temperature. Desirably the composition will be sufficiently stable that 85% of the creatine remains following a period of at least 31 days, more preferably 45 days, and most preferably at least 73 days storage at ambient temperature.

The amount of creatine per Kg of prepared composition may range from 0.5 to 200 g, with a preferred content of about 100 g per Kg. The normal serving size is in the range 25-250 g, providing about 2-5 g (preferably about 3 g) of creatine. During the first 4 days of creatine supplementation the recommended consumption is about 25 g, to achieve creatine saturation. This is followed by 1 serving per day containing about 3 g of creatine to provide a maintenance level of creatine.

The composition of the invention takes the form of a bar, such as a nutrient bar. Bar as used in this application refers to the well-known, solid, individual servings of food products such as nutrient bars, health bars, energy bars, etc. However, the term bar as used in this application is not limited to a specific conventional shape such as an oblong-shaped nutritional bar. A bar product of the present invention is preferably formed like a conventional oblong nutrition bar but can also be produced in the form of a square, disc, or any other shape that might be used to present an individual solid serving of a health, nutrition, or candy product. Each bar will typically have a mass in the range 15-250 g, preferably about 30-75 g. The bars may be individually wrapped, or a plurality of bars may be collectively packaged and wrapped. Suitable packaging and wrapping will be apparent to those skilled in the art. Preferably the wrapping will comprise a layer of moisture-impermeable material, such as a metallised foil or a synthetic plastics material.

Additional optional ingredients of the bar include any one or more of the following: foodstuffs; sweeteners (natural or artificial); flavorings (natural or artificial); raising agent (e.g. sodium bicarbonate and disodium phosphate); lipids; binding agents; preservatives; vitamins; and minerals. Additionally the optional ingredients of the bar may contain protein concentrates or isolates such as soy, whey and caseinates.

Preferred foodstuffs include: fruit (e.g. sliced, dried bananas; glacé cherries; citrus fruit peel or zest); cereals (e.g. oats, wheat); nuts (e.g. peanuts, cashew nuts, hazelnuts)—whole, crushed or pasted; and chocolate chips.

Preferred sweeteners include: sucrose or glucose powder; syrups (e.g. glucose syrup, corn syrup); aspartame; acesulfam K; saccharine or sucralose.

Preferred flavorings include: salt; and fruit flavors, such as berry, lemon, orange, papaya and grapefruit.

Preferred preservatives include: potassium sorbate and potassium benzoate.

Preferred vitamins and minerals include: dicalcium phosphate, dipotassium phosphate, magnesium oxide, monocalcium phosphate, ascorbic acid, ferric orthophosphate, vitamin E acetate, niacinamide, zinc oxide, copper gluconate, d-calcium pantothenate, manganese sulfate, vitamin A palmitate, pyridoxine hydrochloride, thiamin mononitrate, riboflavin, sodium molybdate, chromium chloride, folic acid, biotin, sodium selenite, potassium iodide, vitamin K1 (phytonadione), and vitamin B12.

The mineral and trace elements can also be added in any type or form which is suitable for human consumption. It is convenient to provide the calcium and potassium in the form of their gluconates, phosphates or hydrogen phosphates, and magnesium as the oxide or carbonate, chromium as chromium picolmate, selenium as sodium selenite or selenate, and zinc as zinc gluconate. Typically the amounts are:—sodium at 400 mg/Kg, calcium at 100 mg/Kg, chloride at 600 mg/Kg, potassium at 200 mg/Kg, magnesium at 75 mg/Kg and phosphorus at 50 mg/Kg, chromium at 125 µg/Kg, selenium at 125 µg/Kg and zinc at 15 mg/Kg.

It may also be preferred to include carbohydrates sources which have a low glycemic index, such as fructose, maltitol, glycerin, and cereals such as oats. The glycemic index is a measure of the ability of a nutrient to raise blood glucose levels after ingestion and is defined as the incremental area under the blood glucose response curve of a 50 g carbohydrate portion of a test food expressed as a percent of the response to the same amount of carbohydrate as pure glucose taken by the same subject (The Glucose Revolution. The Authoritative Guide to the Glycemic Index. J. Brand-Miller et al., Marlowe and Co., New York, 1999). A low glycemic index is defined as any index of 55 or below. Such substances are especially useful in foodstuffs intended for consumption by diabetics or for those seeking to lose weight. The combination of creatine with carbohydrates with a low glycemic index is contrary to current commercial practice (WO96/183139). Commercial products combining creatine with carbohydrate emphasize the use of those with a high glycemic index which stimulate the release of insulin. This is recommended as insulin has been shown to increase the uptake of creatine into muscle at least in the early stages of creatine loading. However, for athletes, sports persons and individuals in active training, sudden increases in the blood glucose concentration can have a detrimental effect on exercise performance if this leads to excessive insulin release followed by rapid uptake of glucose by peripheral tissues. Others wishing to avoid increased levels of glucose in the circulation or elevations of insulin will also avoid the use of foods and nutrients with a high glycemic index.

Other preferred ingredients include: emulsifiers (e.g., soya lecithin). Preferably the bar may also comprise a coating, which improves one or more of the appearance, flavor and texture of the bar. Preferred coatings include chocolate-flavored coatings (white or dark chocolate) and yoghurt.

Trials have shown that creatine saturation of muscle in humans can be achieved by consumption of a 'loading' dose of creatine in the range 20-35 g creatine over 4-5 days and thereafter creatine saturation can be maintained by consumption of a lower 'maintenance' dose of 2-10 g (preferably 3-5 g) creatine per day.

The creatine content of a nutrient bar in accordance with the invention will conveniently be such as to provide a maintenance dose of creatine in a single bar of about 15-75 g in mass, and a loading dose of creatine provided by consumption of several such bars or by consumption of a smaller number of larger bars (e.g. a 75-150 g size). Typically the creatine content of the bar will be 0.25 g-15 g, more preferably 3-5 g for a bar of 15-75 g, and 6-10 g of creatine for a bar of 75-150 g size.

It is preferred that the overall water content of the bar is low (i.e., less than 20% w/w, preferably less than 15%, more preferably less than 10%), such that the creatine content of the bar substantially remains in solid form and does not become dissolved, thereby preventing the conversion of creatine to the inactive compound creatinine. Alternatively, if the overall water content of the bar is greater than 20%, it is preferred that the creatine is provided in a discrete portion or layer of the bar in which the water content is less than 20%, and wherein ingress of moisture into said portion or layer is substantially prevented (e.g. by provision of an edible, water-impermeable coating).

The bars may be eaten as a snack, or a large bar or plurality of smaller bars eaten as a meal replacement (preferably with a beverage such as water, tea, coffee etc).

The bars may be formed by any convenient method e.g. cutting, molding, and/or extruding.

One typical embodiment of the invention takes the form of a bar comprising a cereal, solid creatine, sweetener, one or more flavorings, raising agent and margarine. The ingredients are mixed, briefly baked, cooled and then cut into bars. An alternative embodiment (suitable for manufacture by extrusion) takes the form of a smooth, semi-solid mixture comprising protein (e.g., soya isolate, whey protein, caseinate, or other milk- or soya-derived proteinaceous product), solid creatine, a sweetener and glycerin or a syrup.

In a second aspect, the invention provides a method of making a creatine-containing nutrient bar for human consumption, the method comprising the steps of: mixing solid creatine with an edible supporting matrix; forming the resulting mixture into a bar; and packaging the bar.

Typically, the solid creatine will be mixed with other solid components before being mixed with the edible supporting matrix. A preferred edible supporting matrix comprises butter, margarine or other fat which is conveniently melted to facilitate mixing with the creatine and other solid ingredients which may optionally be present. Preferably the edible supporting matrix also functions as a binding agent, serving to bind the ingredients together.

The mixed ingredients may be subjected to further processing steps, e.g., baking, whipping, cooling, etc. The preferred manner in which the mixed ingredients are formed into a bar may depend, at least in part, on the physical properties of the composition. Thus, for instance, some compositions may be formed into bars by extrusion through a die of suitable size and shape, and then cutting the extruded composition into desired lengths. Alternatively the composition may be allowed to harden in molds, or may be baked and cut.

Once formed, the bars may be packaged in any desired manner (e.g., singly or in packets). Preferably the packaging will comprise the step of providing a moisture impermeable wrapping (e.g., a metallic foil or a synthetic plastics material) around a bar or plurality of bars. Such methods are well known to those skilled in the art.

The present invention is demonstrated by the following non-limiting examples.

EXAMPLE 1

An oat based cooked bar with high energy content containing at least 5 grams Creatine monohydrate per bar.

| Ingredients (per 100 g) | |
|---|---|
| Oats | 40 g |
| Partially inverted refined syrup | 30 g |
| Margarine | 23 g |
| Creatine monohydrate (micronised) | 5.5 g |

-continued

| Ingredients (per 100 g) | |
|---|---|
| Raising agent (e.g. sodium bicarbonate; disodium phosphate) | 0.5 g |
| Flavoring, potassium sorbate | 1 g |

| Nutritional profile | |
|---|---|
| Energy | 415 kcal |
| Protein | 5 g |
| Carbohydrate | 57 g |
| Fat | 19 g |
| Fibre | 4 g |

Optional Additional Flavorings
  (i) Cherry Flavor
    Add: glacé cherries 6%
  (ii) Banana
    Add: dried bananas (24%), wholemeal flour, sugar, hazelnuts
Optional Additional Coatings
  (iii) White Chocolate flavor
    Add: white chocolate flavor coating 10% (sugar, hydrogenated vegetable oil, whey powder, wheat flour, palm oil, emulsifier, flavoring).
  (iv) Chocolate Flavor
    Add: chocolate flavor coating 10% (sugar, hydrogenated vegetable oil, whey powder, milk solids, lactose, palm oil, fat reduced cocoa powder, emulsifiers, flavoring).
  (v) Yoghurt Flavor
    Add: yoghurt flavor coating 10% (sugar, hydrogenated vegetable oil, yoghurt powder, whey powder, wheat flour, palm oil, emulsifier, flavoring).
Method of Manufacture The margarine is melted by gentle heating and added to the syrup and well mixed in a suitable commercial mixer. The dry ingredients (oats, creatine monohydrate, raising agent) are mixed separately and then added to the liquid and well mixed. The whole mix is placed in a tray about 1 inch deep and placed in a hot oven at 250° C. for 6 min. It is then allowed to cool to room temperature and cut into 100 g pieces. These are then wrapped in foil or any other suitable food containment/storage wrapping material.

Additional Flavorings

For the cherry and banana flavors the appropriate amounts of additional ingredients are added to the basic mix and the amount of creatine monohydrate is adjusted pro-rata to give a final concentration of 5% w/w.

Coatings

The appearance of the bar is vastly improved by coating it with a desirable edible coating such as chocolate or yoghurt. This is applied after the cooked mass cooled and cut up into bars. The melted coating is applied to each bar to increase its weight by about 10% and the bar is placed in a cooling tunnel before wrapping.

Creatine Content

After manufacture a sample of bars without additional flavoring and uncoated were analyzed for creatine content. The loss of creatine during processing was negligible (see example 4). During subsequent weeks the creatine content remained remarkably stable at room temperature.

EXAMPLE 2

An extruded chocolate bar containing about 3 g creatine.

| Ingredients (per bar) | |
|---|---|
| Protein Blend | 20 g |
| (Whey Protein Isolate, Soy Protein Isolate, Calcium Caseinate), | |
| Sucrose | 20 g |
| Glycerin | 5.5 g |
| Creatine monohydrate | 3 g |
| Glucose syrup, Cocoa Liquor, Cocoa Powder, Natural & Artificial Flavors, | 1 g |
| Soya Lecithin | 1 g |
| Water | 1 g |
| Sucralose | 0.25 g |

Chocolate Coating (10% Mass of Bar)
  Maltitol, partially fractionated Palm kernel oil, whey protein concentrate, cocoa powder, calcium carbonate, natural flavor, soya lecithin sucralose.

| Nutritional profile (per bar) | |
|---|---|
| Energy | 160 kcal. |
| Protein | 15 g |
| Carbohydrate | 25 g |
| Fat | 5 g |

Manufacture

The dry ingredients and the liquid ingredients are mixed separately and then added together with further mixing. The whole is then extruded at room temperature and cut into bars. The chocolate coating is heated and applied, the bars cooled and wrapped.

EXAMPLE 3

Extruded chocolate bar containing at least 3 g creatine, with a low glycemic index containing vitamins and minerals.

| Ingredients (per bar) | |
|---|---|
| Protein Blend | 20 g |
| (whey protein isolate, soy protein isolate, calcium caseinate) | |
| Maltitol | 20 g |
| Glycerin | 5 g |
| Creatine monohydrate | 3.3 g |
| Brown Rice Syrup | 2 g |
| Cocoa Liquor, Cocoa Powder, Natural & Artificial Flavors | 1 g |
| Soya Lecithin | 1 g |
| Water | 1 g |
| Sucralose | 0.7 g |
| Vitamin mix* (containing 10% RDA) | 1 g |

*Vitamins and Minerals included in mix: dicalcium phosphate, dipotassium phosphate, magnesium oxide, monocalcium phosphate, ascorbic acid, ferric orthophosphate, vitamin E acetate, niacinamide, zinc oxide, copper gluconate, d-calcium pantothenate, manganese sulfate, vitamin A palmitate, pyridoxine hydrochloride, thiamin mononitrate, riboflavin, sodium molybdate, chromium chloride, folic acid, biotin, sodium selenite, potassium iodide, vitamin K1 (Phytonadione), vitamin B12.

Chocolate Coating (10% of Weight)
  Maltitol, partially fractionated palm kernel oil, whey protein concentrate, cocoa powder, calcium carbonate, natural flavor, soya lecithin, sucralose.

| Nutritional Composition (per bar) | |
| --- | --- |
| Energy | 160 kcal |
| Protein | 15 g |
| Carbohydrate | 25 g |
| Fat | 5 g | was added to initiate the assay. Changes in absorbance were compared to those obtained with standards of creatine monohydrate of 0.5 to 2 mM 3. Creatinine was assayed at 500 nM using the alkaline picrate method and the kit (555-A) supplied by Sigma Diagnostics, in 30 μl of diluted extract in a final volume of 280 μl. The difference in absorbance between samples and blanks were compared to those obtained with standards of creatinine of 0.5 to 2 mM.

B) Results are Shown in Table 1

TABLE 1

| Type of Bar | Flavor | $Cr.H_2O$ added per 50 g bar g | Wt of bar g | $Cr.H_2O$ per bar by analysis g | Creatinine per bar by analysis g | $Cr.H_2O$ per 50 g by analysis g | $Cr.H_2O$ per 50 g by calculation g |
| --- | --- | --- | --- | --- | --- | --- | --- |
| 5 g Cr Example 1 pH 7.18 | Plain | 5.0 | 60.21 (58.49**) | 6.087 (0.035**) | 0.062 (0.035**) | 5.055 (5.188**) | 5.122 (5.228**) |
| 5 g Cr Example 1 pH 7.18 | Plain | 5.0 | 58.41 | 5.959 | 0.050 | 5.101 | 5.158 |
| 5 g Cr Example 1 pH 7.18 | Plain | 5.0 | 61.90 | 6.416 | 0.073 | 5.183 | 5.260 |
| 3 g Cr Example 1 pH 7.12 | Plain | 3.0 | 61.14 (60.96**) | 3.900 (3.924**) | 0.070 (0.087**) | 3.189 (3.219**) | 3.265 (3.313**) |
| I-R Example 3 | Peanut | 5.0 | 48.00 | 4.486 | 0.053 | 4.673 | 4.746 |
| I-R Example 3 pH 7.29 | Chocolate | 5.0 | 49.01 (49.01**) | 4.972 (4.846**) | 0.063 (0.112**) | 5.073 (4.943**) | 5.158 (5.094**) |
| I-R Example 3 | Chocolate | 5.0 | 46.99 | 5.083 | 0.079 | 5.408 | 5.519 |

*Sum of creatine by analysis + creatine converted to creatinine
**Second sample of bar analyzed 4 weeks after the first analysis Manufacture The dry ingredients and the liquid ingredients are mixed separately and then added together with further mixing. The whole is then extruded at room temperature and cut into bars. The chocolate coating is heated and applied, the bars cooled and wrapped.

Creatine Content

Analysis of creatine showed a negligible loss of creatine during manufacture (see Example 4). No further loss of creatine occurred even after several weeks at room temperature.

EXAMPLE 4

Analysis of Creatine in Manufactured Bars

A) Method of Analysis

1. Bars were weighed to three decimal places and placed in a blender with 400 ml warm distilled water (dH2O) and homogenized during 3×30 s bursts. The homogenate and washings (prepared using cold dH2O) from the blender were poured into a volumetric flask, made up to 2 liters and mixed over 5 min. A 1 ml sample of the final homogenate was clarified by centrifugation at 10,000 rpm and 250 μl was added to approximately 3 ml of dH2O (exact volume determined by weighing to 4 decimal places).

2. Creatine was measured photometrically at 340 nm by means of a linked enzymic assay, in 25 μl of diluted extract in a final assay volume of 275 μl using a microplate reader. Assays were conducted in the presence of lactate dehydrogenase, pyruvate kinase, 30 mM K+, 10 mM Mg2+, 1 mM EDTA, 1 mM phosphoenolpyruvate, 2 mM adenosine triphosphate, 0.3 mM nicotinamide dinucleotide. Creatine kinase Bars according to Example 1 were first analyzed 4 weeks after manufacture, whilst bars according to Example 3 were first analyzed 2 weeks after manufacture. All bars were stored at room temperature prior to analysis.

C) Conclusions

The results show that very little creatine was destroyed during the manufacture of the bars since the analysis of creatine present is similar to the amount added. Also the amount of creatinine from creatine formed is very small.

What is claimed is:

1. A solid food stuff for human consumption comprising 0.05 wt % to 20 wt % of creatine suspended in solid form in an edible supporting matrix wherein the edible supporting matrix comprises no more than 20% water and carbohydrates having a glycemic index of 55 or less, wherein the solid food stuff as a whole has a glycemic index of 55 or less, and wherein the solid food stuff does not comprise ingredients with a glycemic index of more than 55.

2. A foodstuff according to claim 1, further comprising one or more additional ingredients selected from the group consisting of: fruit; cereals; nuts; cocoa; chocolate; vitamins; minerals; lipids; fibre; flavors; and preservatives.

3. A foodstuff according to claim 1, further comprising one or more protein concentrates.

4. A foodstuff according to claim 3, wherein the protein concentrate is selected from the group consisting of soy protein, whey protein and caseinates.

5. A foodstuff according to claim 1, wherein the edible supporting matrix comprises a spreadable solid.

6. A foodstuff according to claim 5, wherein the spreadable solid comprises butter, margarine or other fat.

7. A foodstuff according to claim 1, further comprising an artificial sweetener.

8. A foodstuff according to claim 7, wherein the artificial sweetener is selected from the group consisting of aspartame, acesulfame k, saccharine and sucralose.

9. A foodstuff according to claim 1, further comprising one or more vitamins and minerals selected from the group consisting of dicalcium phosphate, dipotassium phosphate, magnesium oxide, monocalcium phosphate, ascorbic acid, ferric orthophosphate, vitamin E acetate, niacinaminde, zinc oxide, copper gluconate, d-calcium pantothenate, manganese sulfate, vitamin A palmitate, pyridoxine hydrochloride, thiamin mononitrate, riboflavin, sodium molybdate, chromium chloride, folic acid, biotin, sodium selenite, potassium idodine, vitamin K1 (phytonadione), and Vitamin B12.

10. A foodstuff according to claim 1, wherein said 0.05 wt % to 20 wt % of creatine is at least 5 g creatine.

11. A foodstuff according to claim 1, formed into a bar with a mass in the range of 15-250 g.

12. A foodstuff according to claim 11, formed into a bar with a mass in the range of 30-150 g.

13. A foodstuff according to claim 1, further comprising an edible coating.

14. A foodstuff according to claim 13, wherein the coating comprises a chocolate flavored coating or a yogurt coating.

15. A method of making a creatine containing nutrient bar for human consumption, the method comprising the steps of mixing solid creatine with an edible supporting matrix according to claim 1; physically forming the resulting mixture into a bar, and enclosing the bar in a package.

16. A method according to claim 15, wherein all solid ingredients are mixed together prior to mixing with the edible supporting matrix.

17. A method according to claim 15, wherein the edible supporting matrix comprise butter, margarine or other fat.

18. A method according to claim 15, wherein forming the mixture into a bar comprises the step of extruding and/or cutting the mixture.

* * * * *